United States Patent [19]

Nelson

[11] Patent Number: 4,825,856
[45] Date of Patent: May 2, 1989

[54] REINFORCED ANKLE AND FOOT BRACE

[76] Inventor: Ronald E. Nelson, 405 Sunset La., Cambridge, Minn. 55008

[21] Appl. No.: 152,488

[22] Filed: Feb. 5, 1988

[51] Int. Cl.⁴ .............................. A61F 5/00; A61F 3/00
[52] U.S. Cl. ................................... 128/80 H; 128/581
[58] Field of Search .................... 128/80, 80 G, 80 H, 128/581, 166, 165, 166.5, 586, 588, 595, 622, 589

[56] References Cited

U.S. PATENT DOCUMENTS

| | | | |
|---|---|---|---|
| 260,069 | 12/1882 | Wallace | 111/83 |
| 325,280 | 9/1885 | Smadbeck et al. | 36/89 |
| 332,727 | 10/1885 | McEwen | 128/166 |
| 832,613 | 10/1906 | Krieger | 128/166 |
| 2,318,148 | 5/1943 | Ettelbrick | 128/588 |
| 3,067,531 | 12/1962 | Scott et al. | 36/120 |
| 3,323,232 | 6/1967 | Danowsky | 36/91 |
| 3,327,410 | 6/1967 | Park et al. | 36/89 |
| 3,970,083 | 7/1976 | Carrigan | 128/166 |
| 4,187,844 | 2/1980 | Caprio, Jr. | 128/166 |
| 4,237,874 | 12/1980 | Nelson | 128/80 H |
| 4,280,488 | 7/1981 | Polsky et al. | 128/80 H |
| 4,338,522 | 12/1980 | Potts | 128/90 |
| 4,409,976 | 10/1983 | Pence | 128/80 H |
| 4,527,556 | 7/1985 | Nelson | 128/80 H |
| 4,590,932 | 5/1986 | Wilkerson | 128/80 H |
| 4,638,794 | 1/1987 | Grisar | 128/595 |
| 4,651,726 | 3/1987 | Holland | 128/80 H |
| 4,716,892 | 1/1988 | Brunswick | 128/77 |
| 4,727,863 | 3/1988 | Nelson | 128/80 H |

Primary Examiner—Edgar S. Burr
Assistant Examiner—Kimberly L. Asher
Attorney, Agent, or Firm—Burd, Bartz & Gutenkauf

[57] ABSTRACT

An ankle brace for relative confinement of the foot and ankle to help prevent injury to an individual engaged in active conduct, or inhibit aggravation of pre-existent injury, or provide protection during healing of an injury. A base includes an inner layer of sheet-like material shaped to be engaged in conforming relationship about the foot and ankle. A second layer covers the base. Lateral and medial support panels are embedded on lateral and medial sides of the brace between the inner and second layers. The support panels are formed of a mesh of plastic-type material to conform somewhat to the ankle and lower leg region when the brace in installed and tightly applied to the foot. In one form of the invention, lateral and medial rides are provided with pockets containing removable rigid stay members spanning the area between the lower leg and the upper foot in order to provide greater confinement to the ankle region upon initial healing of an injury. The stays are removable once the healing process is along the way and less restriction is required of the ankle.

32 Claims, 5 Drawing Sheets

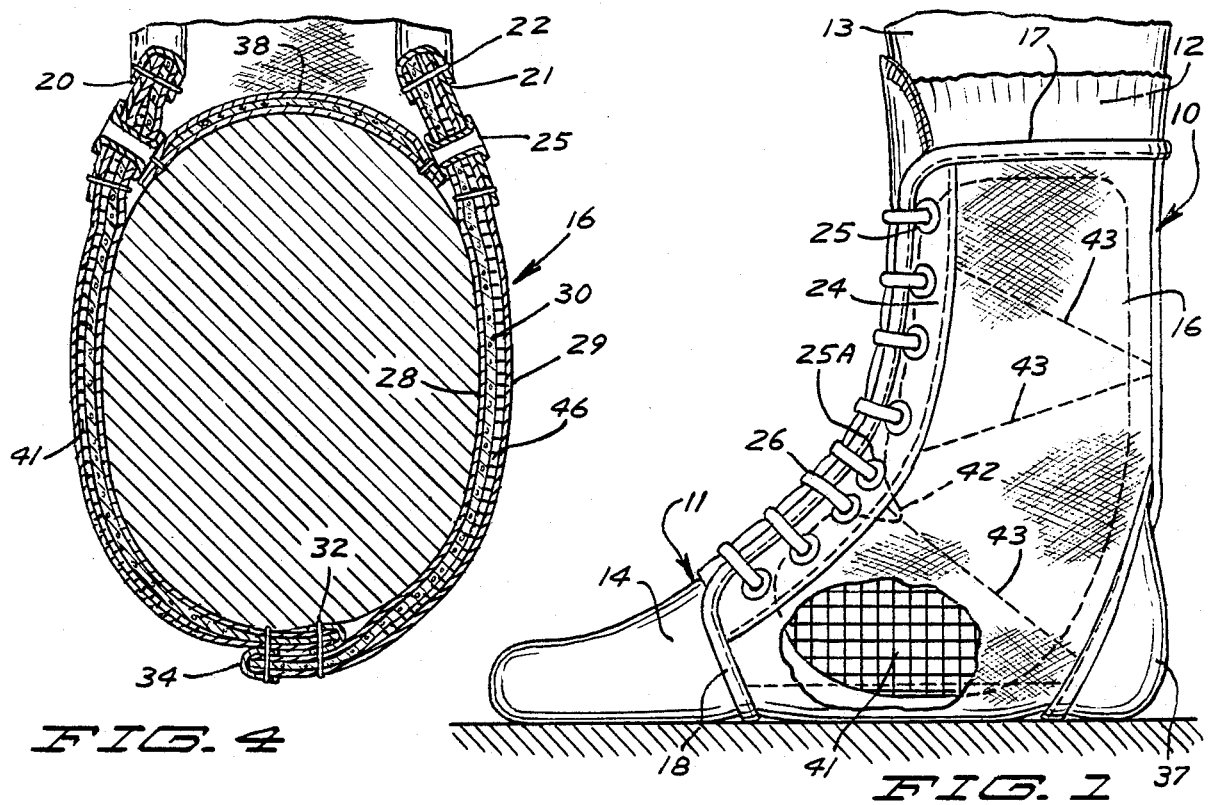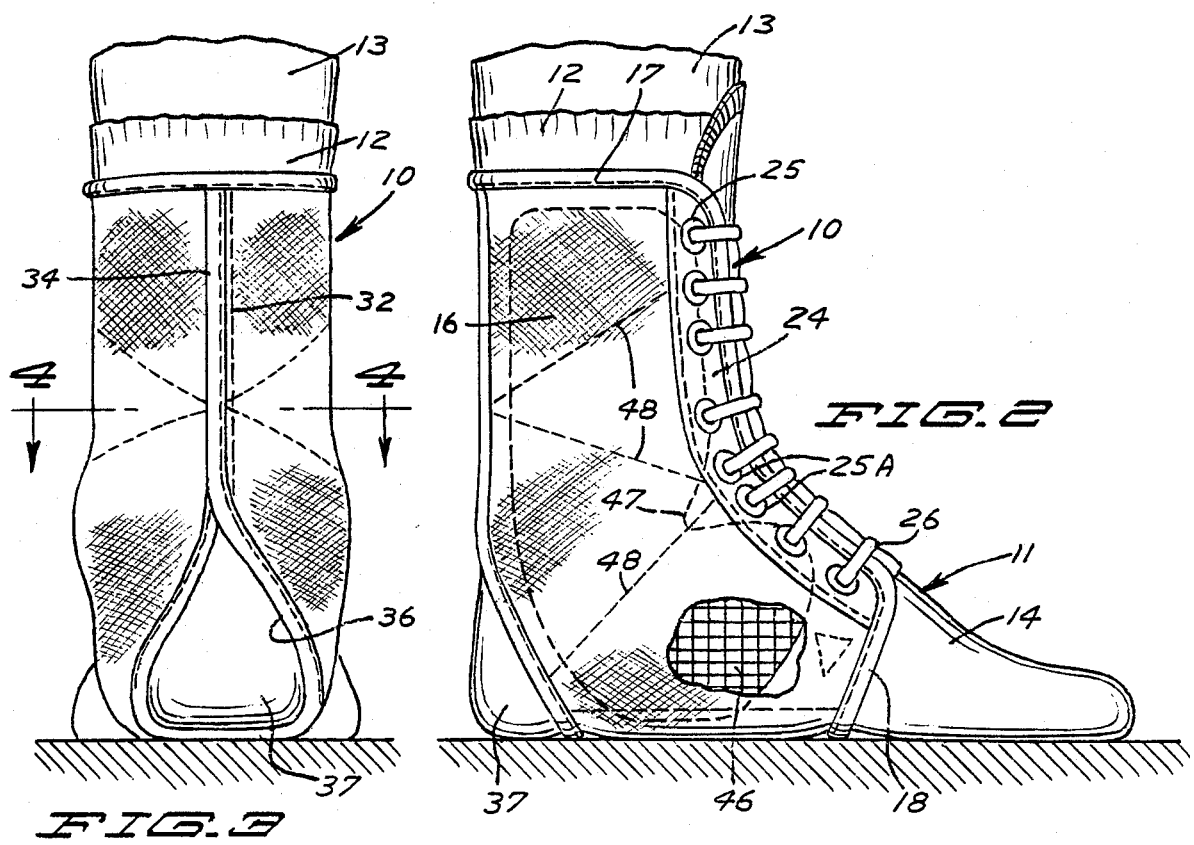

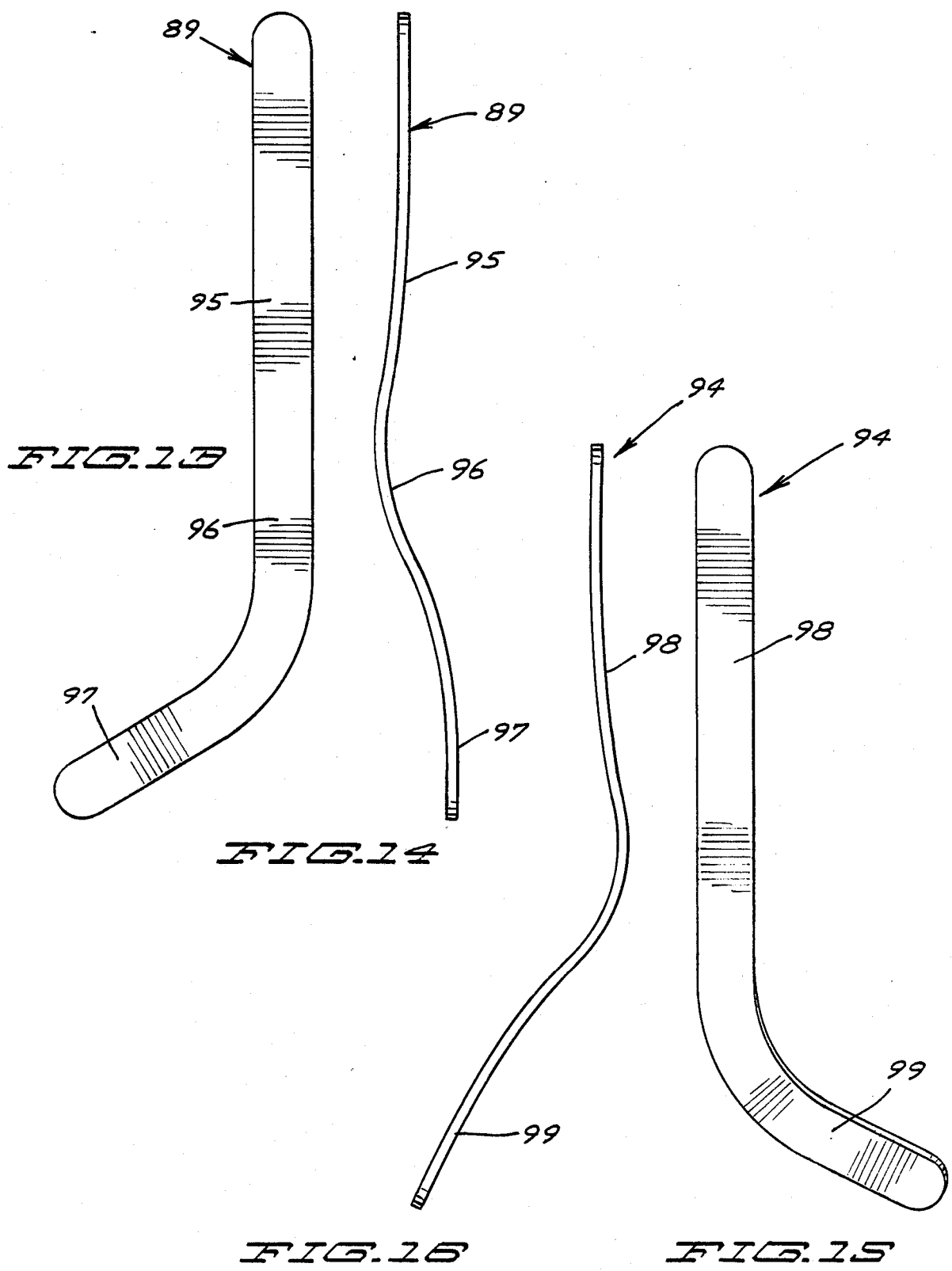

REINFORCED ANKLE AND FOOT BRACE

BACKGROUND OF THE INVENTION

The ankle joint's intended movements are only flexion, also called dorsal flexion, and extension, also called planar flexion. Flexion is movement of the superior surface of the foot toward the anterior surface of the leg. Extension is the reverse action. The two lower leg bones, the tibia and the fibula, join to form the top half of the ankle joint. The ankle is composed of seven bones known as the tarsal bones. One of these is the talus or ankle bone. The fibula and tibia are held tightly together by ligaments and form a mortice for reception of the talus. A relatively complex ligament system holds the ankle joint together. The tibiofibular joints include three separate articulations, namely, the inferior tibiofibular joint which is the articulation between the lateral malleolus and the tibia; the tibiofibular union which is the union of the shafts of the tibia and fibula by an interosseous membrane that consists of numerous short fibers which pass transversely from one articular surface to the other; and the superior tibiofibular articulation which is the articulation between the head of the fibia and the fibular facet of the tibia. Normal movements of these tibiofibular joints consist merely of gliding movements, which are passive in character in that they complement the movements of the ankle joint. Thus, during flexion of the ankle, the fibula tends to be displaced upward. During extension, it is displaced downward. These movements are normally resisted by the interosseous membrane.

The chief traumatic problem associated with the ankle is ankle sprain, usually involving either extreme inversion or extreme eversion. Eighty-five percent of all injuries of the ankle are inversion injuries, in which the foot is forced inward in relation to the leg. In eversion injuries, the foot is forced outward in relation to the leg.

During engagement in a particularly strenuous activity, such as sports, it is advisable to restrain the ankle and tibiofibular joints from movement other than flexion and extension, and to restrain that movement beyond normal limits.

Fracture of the lateral malleolus is a common injury resulting from either a blow from the medial side or sudden torsion. Both lateral and medial malleoli fractures usually result from severe twisting actions, such as those incurred in ski injuries, that cause a rotational shear of the joint. Such injury heals slowly. Protection should be provided to the healing malleoli in addition to local immobilization.

SUMMARY OF THE INVENTION

The invention pertains to an ankle brace adapted to give generalized support to the ankle and deter it from eventful inversion and eversion as well as to inhibit twisting. The brace is usable by the uninjured individual engaged in rugged activities such as sports to aid in the prevention of injury, as well as during the healing of the injury whether or not the individual is engaged in traumatic activity. The brace includes an inner layer or base and a second layer or cover substantially coextensive with the inner layer and fixed to it. Both are configured to be wrapped around in close conforming relationship to the foot with forward edges that come together on the superior foot surface for fastening by suitable means such as laces.

Lateral and medial flexible support panels are imbedded between the inner and outer layers on the lateral and medial sides of the brace. Each support panel is formed of a flexible, sturdy sheet-like member that is relatively inelastic and is conformable to the ankle between the lower leg and upper foot. The outer layer of the brace wraps the support panel in conforming relationship to the ankle region. The lateral and medial support panels are held in close conformance to the ankle region and inhibit undue movement of the foot with respect to the ankle in directions of inversion and eversion, as well as twisting.

In one form of the invention, elongate, generally upright narrow pockets with open tops are formed on the lateral and medial sides of the brace. Rigid stay members are curved to conform to the anatomical structure of the ankle region. The rigid stay members are inserted in the pockets through the open tops to a position where they fit over the lateral and medial malleoli of the foot, extending above and below that region. The stay members tend to immobilize to the ankle. The stay members are used for purposes of securing an injured ankle during the initial process of healing. Once the ankle is well along the healing process, the rigid stay members are removed from the pockets, leaving the brace intact with the lateral and medial support panels during the remaining healing process and permitting a greater measure of movability of the ankle region.

In the Drawings

FIG. 1 is a medial side elevational view of a foot wearing an ankle brace according to the present invention partly fragmented for purposes of illustration;

FIG. 2 is a lateral side elevational view of the foot and ankle brace of FIG. 1 partly fragmented for purposes of illustration;

FIG. 3 is a rear elevational view of the foot and ankle brace of FIGS. 1 and 2;

FIG. 4 is an enlarged sectional view of the ankle brace of FIG. 3 taken along the line 4—4 thereof;

FIG. 13 is a side elevational view of a lateral stay of the ankle brace of FIG. 7;

FIG. 14 is an end elevational view of the lateral stay of FIG. 13;

FIG. 15 is a side elevational view of a medial stay of the ankle brace of FIG. 7; and FIG. 16 is an end elevation of the medial stay of FIG. 15.

DESCRIPTION OF PREFERRED EMBODIMENTS

Figure 5:
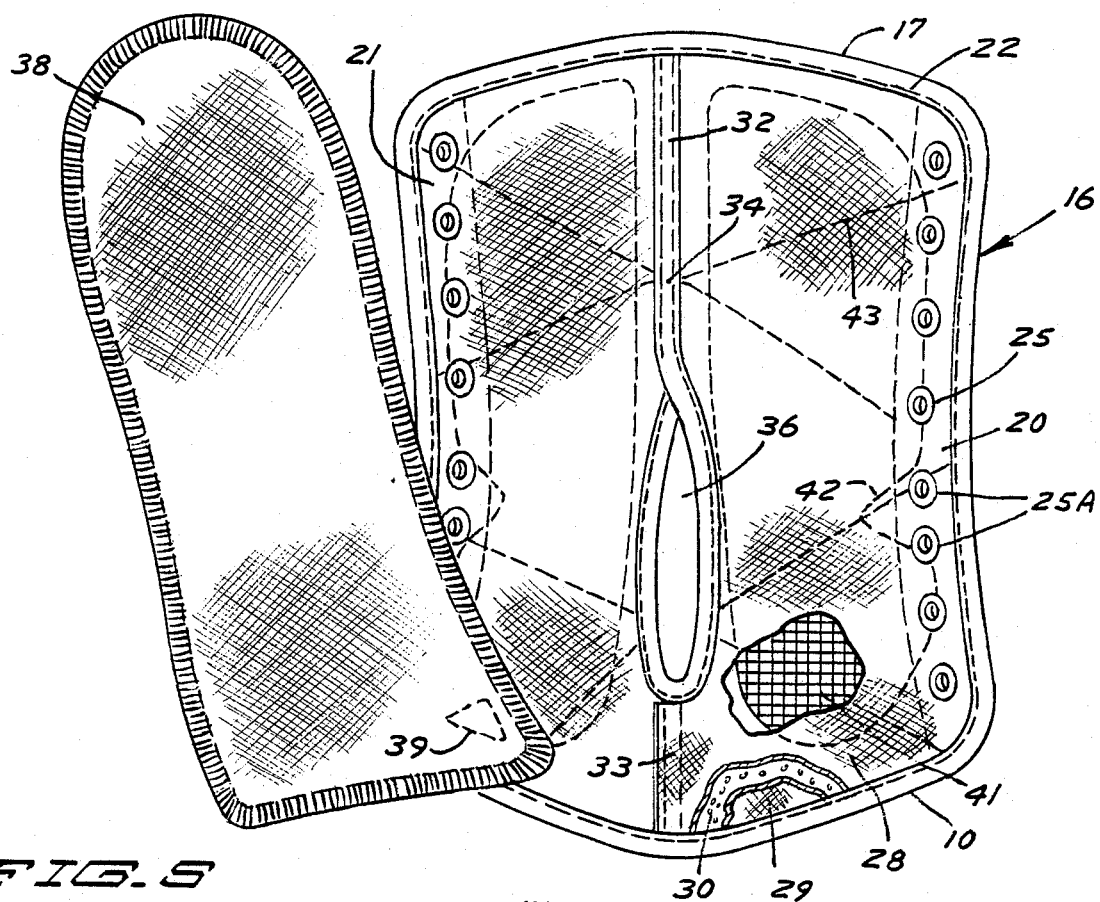
FIG. 5 is a front plan view of the ankle brace of the invention with laces removed and in a spread open configuration to show the inside thereof.

Referring to the drawings, there is shown in FIGS. 1 through 6 an ankle brace indicated generally at 10 installed on a foot 11 optionally wearing a sock 12, extending from the lower leg 13 spanning the ankle and in covering relationship to the mid foot 14. Ankle brace 10 is worn in snug covering relationship to the foot and ankle in order to inhibit inversion and eversion of the ankle as might cause injury to it or aggravate pre-existent injury, as well as inhibit undue twisting of the ankle at the ankle joint. Ankle brace 10 can take the place of the normal ankle or foot wrap or tape. It is much more convenient to apply, and ultimately less expensive than repeated adhesive taping procedures. Additionally, ankle brace 10 is readily removable without discomfort as compared to adhesive tape.

Figure 6:
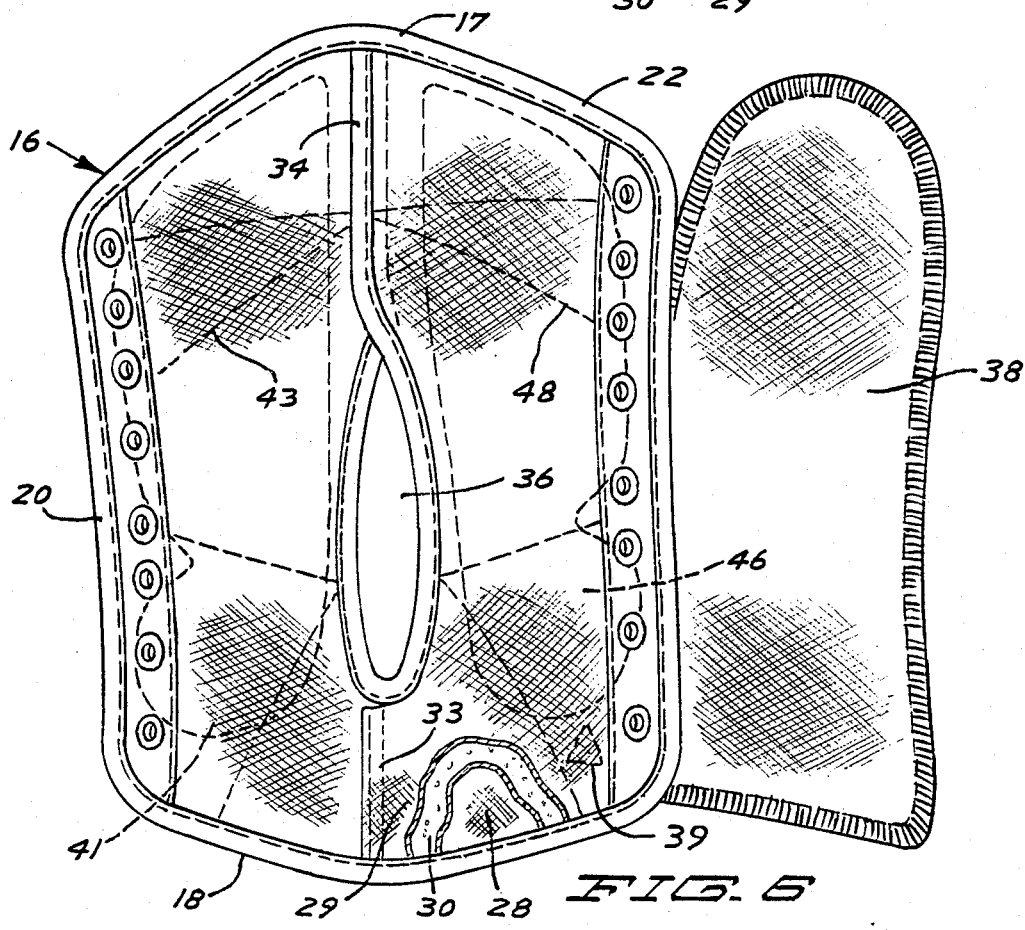
FIG. 6 is a rear plan view of the ankle brace as shown in FIG. 5.
Figure 10:
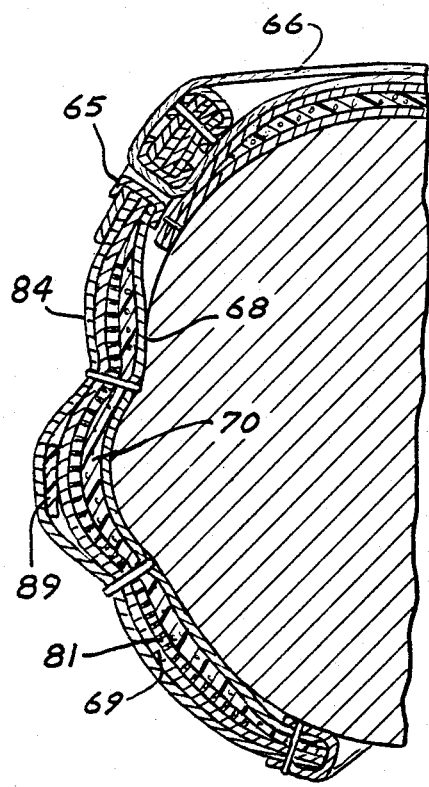
FIG. 10 is an enlarged sectional view of a portion of the ankle brace of FIG. 7 taken along the line 10—10 thereof.

As shown in FIGS. 5 and 6, the ankle brace 10 includes a flexible composite base 16 adapted to be wrapped around the foot and ankle in close conforming relationship to them. Base 16 has an upper edge 17 that wraps around the lower leg 13 forming a top opening to brace 10 when base 16 is installed on a foot. A lower edge 18 wraps around the mid foot 14 to form a front opening. Forward edges 20, 21 come toward one another over the front superior foot surface for fastening by suitable means. A continuous edge binding 22 is sewn to the various edges. Reinforcing strips 24 (FIGS. 1 and 2) are fixed to the forward edges 20, 21 and carry eyelets 25. A common lace 26 is trained through the eyelets 25 to hold the forward edges 20, 21 in place toward one another and bind the base 16 on the foot. The middle eyelets 25A are bunched more closely together than the others to provide greater support at that portion of the foot's superior surface where more flexure occurs.

Base 16 includes an inner layer or liner 28 and a substantially coextensive second layer or cover 29 fixed to the inner layer 28 as by edge stitching associated with the binding 22. These layers are formed of a strong, flexible material such as canvas or vinyl. A foam layer 30 can be interposed between the inner and outer layers 28, 29 for purposes of comfort of the wearer. Both layers 28 and 29 are formed of symmetrical half sections that are sewn together by a seam which becomes a rear vertical seam 32 and a short horizontal seam 33 when worn on the foot. Both the seams 32 and 33 are covered by a suitable binding material 34. The horizontal seam 33 and vertical seam 32 are separated by a heel opening 36 for accommodating the heel 37.

A tongue 38 is fixed to the inside of base 16 proximate the lower end of one of the forward edges 21 by a suitable pivot stitch 39. The tongue 38 is adapted to cover the usual foot, ankle and lower leg proximate front edges 20, 21.

Flexible support means are imbedded on lateral and medial sides of base 16 between the outer and inner layers 29, 28. The purpose of the flexible support means is to stiffen the sides of base 10 so as to work against undue inversion, eversion and twisting of the ankle, while still permitting a degree of mobility to the foot. As shown in FIG. 1, a medial support means is comprised as medial support panel 41 of strong, plastic-like material fixed between the inner and outer layers 28, 29 of the medial side of base 16. Panel 41 is sheet-like and formed of a strong, plastic-like material. Panel 41 is formed of a network or grid of interconnected plastic strands forming a high porosity mesh. One set of parallel, spaced apart strands is perpendicuar to a second set forming a symmetric array of open rectangles. The plastic strands are longitudinally inelastic and individually flexible in all directions but confined in the grid to flexure about axes parallel to the local plane of the grid but not perpendicular to it. Support panel 41 has a porosity or ratio open area to total area equal to or greater than 50 percent. The plastic strands or elements are arranged in a density of approximately six to seven per inch and can have a diameter of approximately 0.07 inch. The outer perimeter of panel 41 has an upper portion that is flat and straight, conforming to the upper portion of the medial side of base 16. The lower portion of panel 41 curves forwardly in the vicinity of the heel 37 according to the anatomical curvature of the foot with respect to the ankle, terminating a short distance behind the forward edge 18 of the base 16. The forward edge of the panel 41 extends close to the forward medial edge 20 of base 16 such that the eyelets 25 are fastened through it. The flexible support panel 41 has a notch 42 formed in the forward edge thereof proximate the forward edge 20 of base 16 in the vicinity where the eyelets 25A are bunched together on the medial foot portion. The notch 42 forms a partial hinge for flexure of the panel 41 at the medial foot portion. This portion experiences significant flexure upon movement of the foot with respect to the ankle.

A plurality of seams or stitches 43 are formed between the inner and outer layers 28, 29 of base 16 and the medial support panel 41. Seams 43 hold the support panel 41 in place. They are formed in a more or less zigzag pattern across the medial side of base 16 to section the support panel 41 and add a degree of rigidity to it. So embedded in the base 16, support panel 41 partially curves around the confronting portions of the foot and leg of the wearer forming a semi-rigid cage-type structure about the foot and ankle, providing a good deal of support and inhibiting flexure of the ankle in unwanted direction or beyond healthy limits.

A lateral flexible support panel 46 is embedded on the lateral side of base 16 between the inner and outer layers 28, 29 in symmetrical relationship to the medial support panel 41. Lateral support panel 46 is formed of the same high porosity grid material. Panel 46 has a relatively straight upper portion and a forwardly curved lower portion in conformance to the anatomical structure of the foot and ankle. A notch 47 is located in the intermediate vicinity of the lateral forward edge 21 where the eyelets 25A are bunched together in the area that experiences the greater amount of flexure. Upon flexion of the foot, an outward bend or ripple in the support panel 46 occurs at notch 47. Flexure of the foot is more easily accomplished than would otherwise occur against the restraint of an unnotched support panel 46. A zigzag pattern of seams or stitches 48 secures the support panel 46 relative to the inner and outer layers 28, 29 of the base 16.

Together the medial and lateral support panels 41, 46 encompass substantially the major portions of the medial and lateral sides of the lower leg, ankle and upper foot portions of the individual wearer. The upper portion of the support panels curve around the lower leg in tube-like fashion, and the lower portions of the support panel conform accordingly to the adjacent ankle and foot portions. The support panels cooperate to form a semi-rigid, cage-type structure to inhibit inversion and eversion of the foot and twisting of the ankle about undue limits. The support panels, formed of the latice work or mesh type structure, do not unduly inhibit normal movement of the foot while providing a good measure of support and protection.

Figure 7:
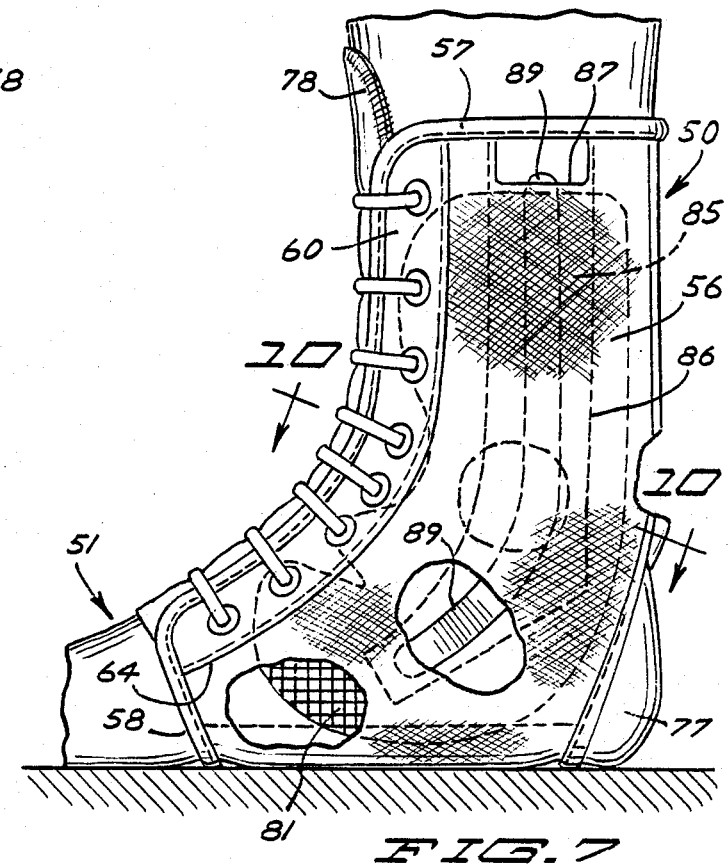
FIG. 7 is a medial side elevational view of a foot wearing an ankle brace according to another form of the invention partly fragmented for purposes of illustration.
Figure 9:
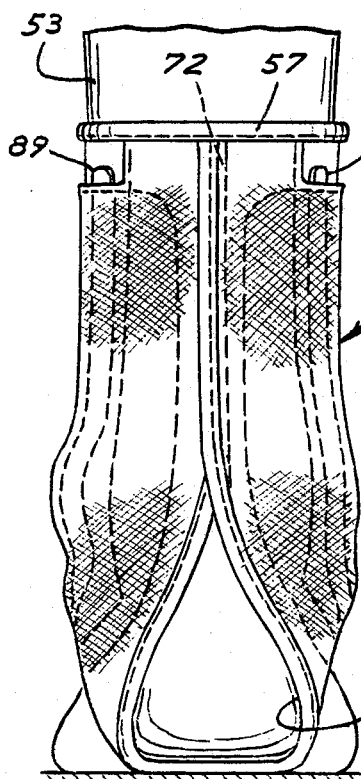
FIG. 9 is a rear elevational view of the foot and ankle brace of FIG. 7.
Figure 8:
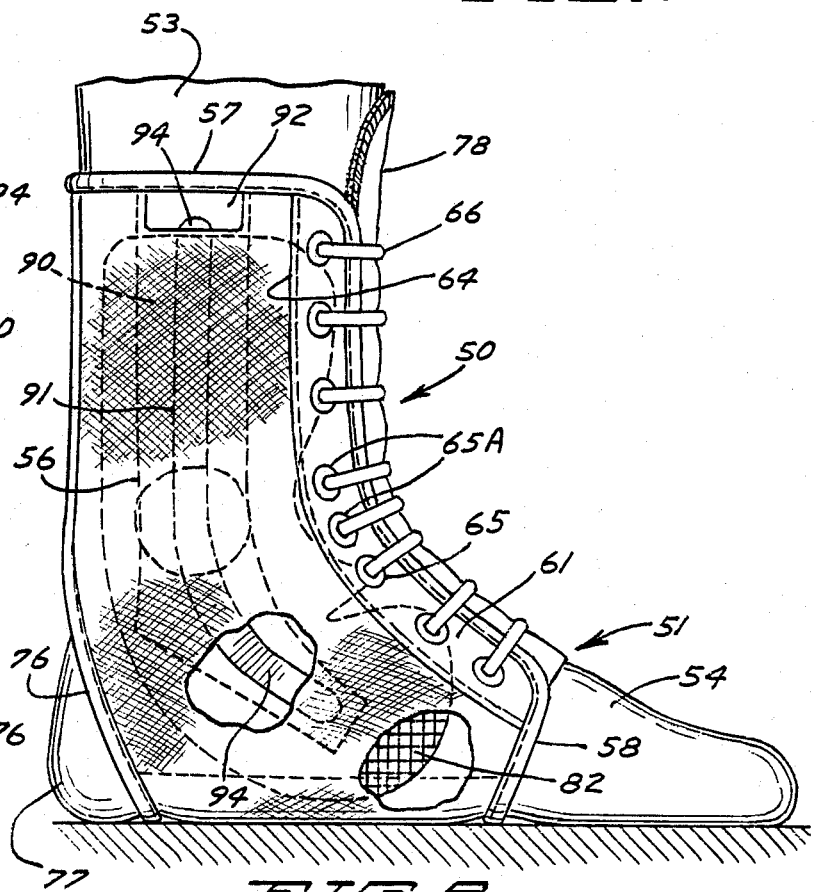
FIG. 8 is a lateral side elevational view of the foot and ankle brace of FIG. 7 partly fragmented for purposes of illustration.
Figure 11:
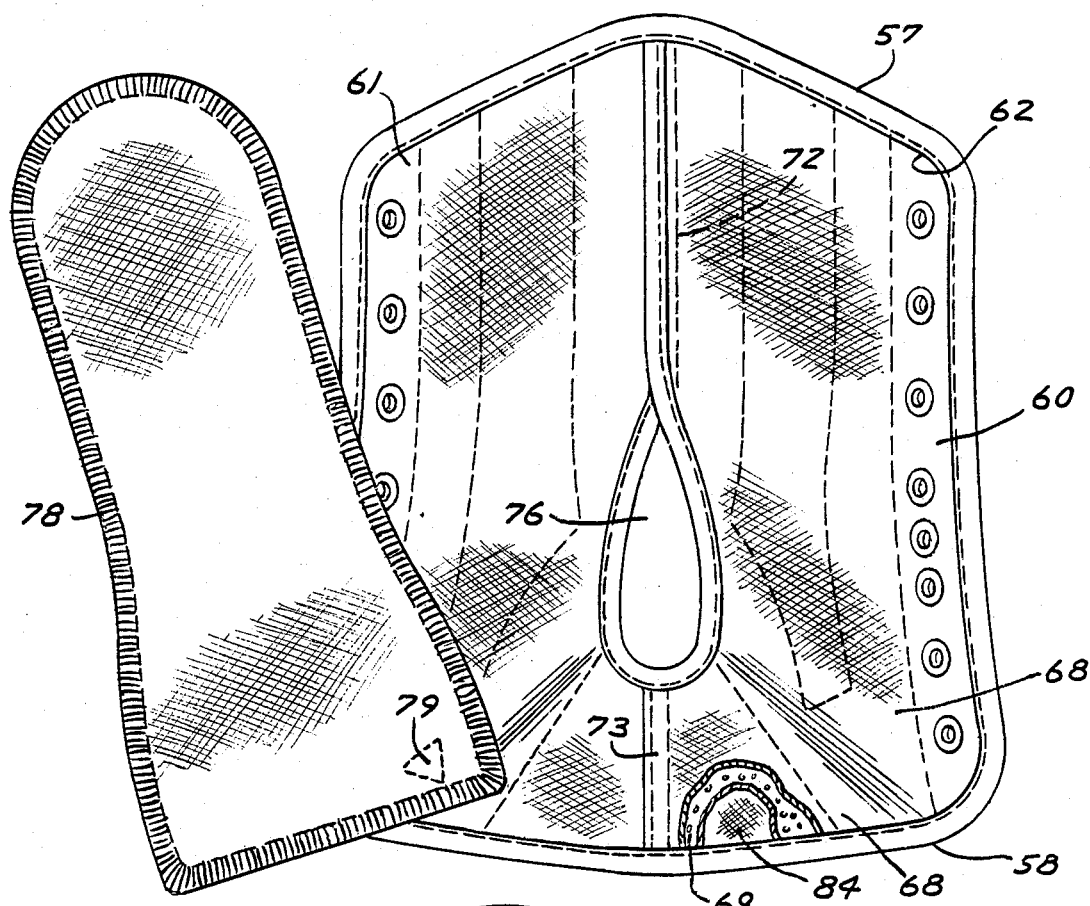
FIG. 11 is a front plan view of the ankle brace of FIG. 7 with laces removed and in a spread open configuration to show the inside thereof.
Figure 12:
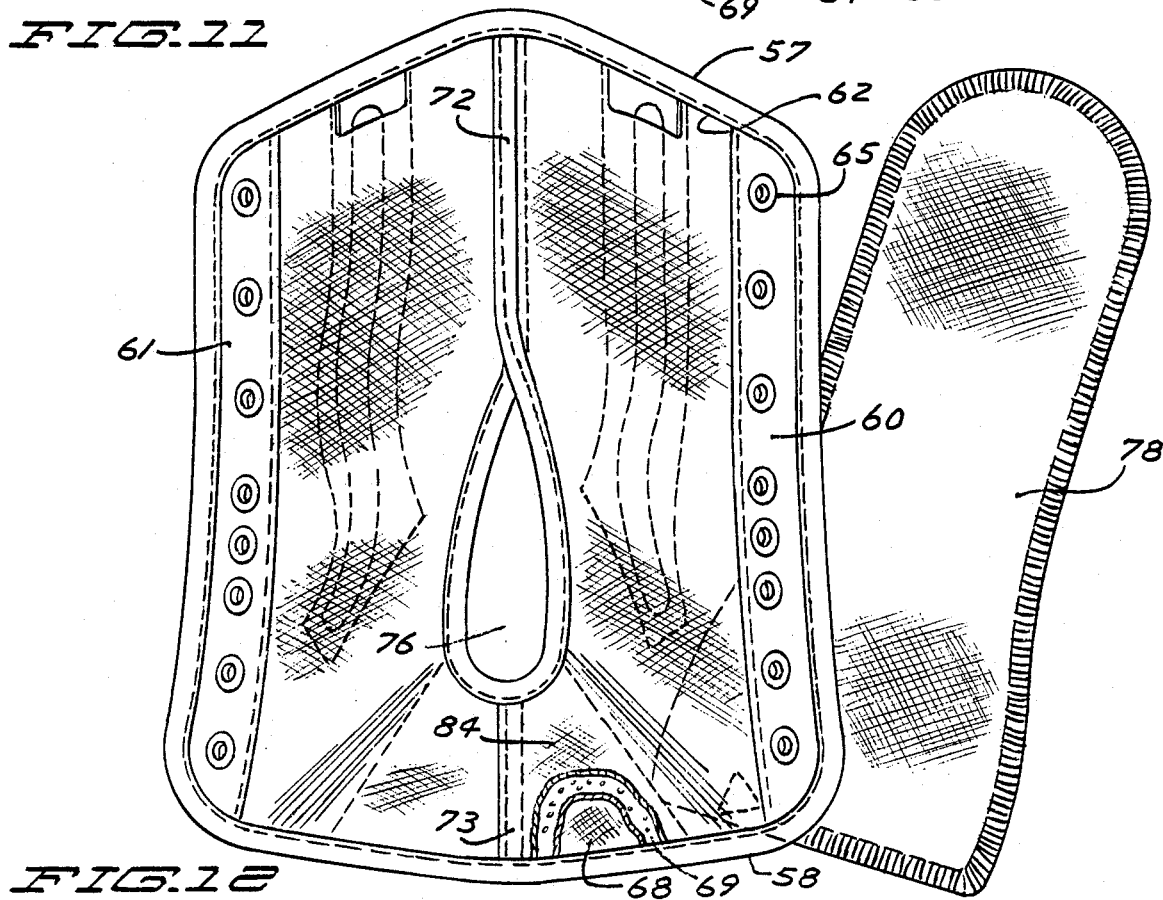
FIG. 12 is a rear plan view of the ankle brace as shown in FIG. 11.

A second form of ankle brace according to the invention is shown in FIGS. 7 through 12 indicated generally at 50. Ankle brace 50 is shown in FIGS. 7 through 9 installed on an injured foot 51 in encompassing relationship to the lower leg portion 53 down to the mid foot portion 54. Brace 50 is usable to confine the ankle region as during initial healing of an injury. Brace 50 includes a base 56 having an upper edge 57 that wraps around the lower leg 53 in conforming relationship forming a top opening to brace 50 when base 56 is installed on a foot. A lower edge 58 wraps around the mid foot 54 to form a front foot opening. Forward edges 60, 61 come together toward one another over the front superior foot surface for fastening by suitable means. A continuous edge binding 62 is sewn to the edges. Reinforcing strips 64 are fixed to the forward edges 60, 61 and carry eyelets 65. Eyelets 65 are more closely bunched together toward the mid portion of the forward edges as at 65A. The eyelets 65 carry a lace 66 in the usual fashion.

Base 56 includes an inner layer or liner 68 and outer layer or cover 69. A foam backing 70 can be integrally attached to the inner layer 68 for purposes of comfort (see FIG. 10). As with respect to the embodiment shown in FIGS. 1 through 6, both the inner layer 68 and the outer layer 69 are formed of symmetrical half sections that are sewn together by a seam which becomes a rear vertical seam 72 and a short horizontal seam 73 when worn on the foot, the seams 72 and 73 being separated by a heel opening 76 for accommodating a heel 77 of the foot 51.

A tongue 78 is fixed to the inside of base 56 proximate the lower end of one of the forward edges 61 by a suitable pivot stitching 79. The tongue 78 is adapted to cover the front portion of the foot, ankle and lower leg located between the front edges 60, 61 of base 56 in usual fashion.

A medial support panel 81 is embedded between the inner and outer layers 68, 69 on the medial side of base 56. A lateral support panel 82 (FIG. 8) is embedded between the inner and outer layers 68, 69 of base 56 on the distal side of base 56. The medial and lateral support panels 81, 82 are positioned with respect to the inner and outer layers 68, 69 like those shown in the ankle brace configuration of FIGS. 1 through 6. The support panels are formed of the same mesh of plastic-like material and function in the same way.

A second outer layer 84 of a durable, flexible material such as vinyl or canvas is installed on base 56 in covering relationship to the first outer layer 69. The purpose of the second outer layer 84 is for the formation of lateral and medial pockets for retention of rigid stay members positioned in confining relationship to the ankle joint during the initial phase of the healing process. A narrow, elongate, open-top medial pocket 85 is formed by stitching 86 between the second outer layer 84 and the first outer layer 69 on the medial side of base 56. Pocket 85 has a straight vertical upper portion and curves forwardly at the lower portion in the direction of the foot. Stitching 86 forming pocket 85 passes through the first outer layer 69, the support panel 81 and the inner layer 68 as well. This serves also to hold the support panel 81 in proper position with respect to the foot and ankle. The pocket 85 has an open top 87 spaced from the upper edge 57 of the base 50. A medial stay member 89 fits in the medial pocket 85. Stay member 89 extends downwardly from the lower leg, and curves forwardly toward the foot at the lower end. Stay member 89 is removable through the open top 87 of pocket 85.

As shown in FIG. 8, a lateral pocket 90 is formed on the lateral side of base 56 by stitching 91 passing through the second outer layer 84 and first outer layer 69, as well as inner layer 68 holding the lateral support panel 82 in proper position. The lateral pocket 90 also has a relatively straight upper portion and curves forwardly in the foot region. Pocket 90 has an open top 92 and contains a rigid lateral stay member 94. The rigid stay 94 is removable from the pocket 90 through the top opening 92. Rigid stay 94 has a relatively straight top portion and a curved lower portion in conformance with the anatomy of the foot.

Rigid medial and lateral stays 89, 94 are curved or contoured to conform to the anatomical structure of the foot and ankle region. The medial and lateral stays are contoured differently due to the dissymmetry of the foot. As shown in FIGS. 13 and 14, medial stay 89 has a relatively straight upper portion 95 in side view that curves forwardly at the lower portion 97. In end view, the intermediate portion curves or is bowed outwardly in a region 96 to be located over the medial malleolus. Below the outward bow, the stay again curves inwardly to encompass the foot depression beneath the medial malleolus. The lateral stay 94, as shown in FIGS. 15 and 16, also has an upper relatively straight portion 98 in side view and a lower forwardly curved portion 99. In end view, the portion 98 leads to an outwardly bowed region curved to conform to the lateral malleolus. The lateral malleolus is located slightly ahead of the medial malleolus such that the bow of the lateral stay member 94 terminates in an inwardly directed portion which fits in a foot depression somewhat greater than on the medial side. This is reflected in the greater amount of curvature at the terminal point of the bow and inward position of the lower end 99 of the lateral stay 94. The medial and lateral stays 89, 94 can be bent to conform closely to the individual foot upon which the base 56 is placed.

In use, the ankle brace 50 is intended for use upon a foot and ankle region which has experienced an injury requiring a sustained period of healing. During the initial healing period the ankle brace 50 is worn upon the foot and ankle with the rigid stay members 89, 94 in place in the pockets 85, 90. The stays are shaped to conform to the anatomical region of the foot. When laced up tightly with the base 56, the brace closely conforms to the anatomical of the foot and ankle. The support panels 81, 82 lend a good deal of support to the ankle. The rigid stay members 89, 94 tend to substantially restrict the mobility of the foot and ankle during the initial healing process. Once the process of healing is well under way, such that greater flexure is permissible, the rigid stays 89, 94 are removed from the pockets 85, 90. The brace 50 still supports the foot and ankle region, but permits a greater measure of mobility under the confinement provided by the support panels 81, 82.

While there has been shown and described certain preferred embodiments of the invention, it is apparent that deviations can be had without departing from the scope and spirit of the claims.

The embodiments of the invention in which an exclusive property or privilege is claimed are defined as follows:

1. An ankle brace to be worn on a foot and ankle in encompassing relationship to the medial and lateral sides of the ankle and proximal foot respectively, comprising:
   a base including an inner layer of flexible sheet-like material shaped to closely encompass the ankle and proximal foot on the forward, rearward, medial and lateral sides thereof;
   a second layer of flexible sheet-like material secured to the inner layer and coextensive therewith at least in the vicinity of the ankle and the adjacent anatomical portions above and below the ankle;
   a medial support panel embedded between the inner layer and the second layer on the medial side of the base positioned to be in covering relationship to the ankle region on the medial side of the foot spanning the area above, below, forward and reward of the ankle when the base is installed on a foot;
   a lateral support panel embedded between the inner layer and the second layer on the lateral side of the base positioned to be in covering relationship to the ankle region on the lateral side of the foot spanning the area above, below, forward and reward of the ankle when the base is installed on a foot;
   medial stitch means on the medial side of the base between the inner layer and the second layer and the medial support panel, said medial stitch means extending back and forth across intermediate portions of the medial support panel between opposite edges thereof in order to hold the medial support panel in place;
   lateral stitch means on the lateral side of the base between the inner layer and the second layer and the the lateral support panel, said lateral stitch means extending back and forth across intermediate portions of the lateral support panel between opposite edges thereof in order to hold the lateral support panel in place;
   each support panel being a sheet-like member formed of a strong relatively inelastic flexible mesh material having a high porosity and resiliently bendable about an axis parallel to the plane of the sheet member.

2. The ankle brace of claim 1 wherein: said inner layer and second layer are coextensive throughout in forming said base, said base having first and second forward edges that come together over the top of the foot and forward of the ankle toward one another, closure means for fixing the first and second forward edges with respect to one another when installed over the foot, said base having a top edge that closes around the lower leg portion and a lower edge that closes around the lower foot when the forward edges are brought together.

3. The ankle brace of claim 2 wherein: said medial and lateral support panels each have a notch located forward of the ankle joint when the base is installed upon a foot.

4. The ankle brace of claim 2 wherein: said medial and lateral stitch means includes zigzag patterns of seams formed on the lateral and medial sides of the base between the inner and second layers to hold the lateral and medial support panels in place.

5. The ankle brace of claim 4 wherein: each support panel is shaped with a relatively straight upper portion extended from beneath the upper edge of the base to a position beneath the ankle in spanning relationship to the ankle, and forwardly curved at the lower portion to follow the contour of the foot.

6. The ankle brace of claim 5 wherein: each said support panel has a notched portion where it begins the forward curvature to follow the contour of the foot.

7. The ankle brace of claim 6 wherein: each support panel is formed of plastic.

8. The ankle brace of claim 6 wherein: each support panel is formed of a grid work comprised of a first set of plastic strands and a second set of plastic strands interconnected to and perpendicular to the first set of plastic strands forming a mesh with a porosity greater than fifty percent and a density approximately between five and eight strands per inch.

9. The ankle brace of claim 1 including: an outer layer of flexible sheet-like material secured to the second layer in encompassing relationship to the second layer at least on the medial and lateral sides of the base; an elongate, narrow medial pocket fromed between the second layer and the outer layer on the medial side of the base extending from a location near the upper edge of the base downwardly to a position beneath the medial malleolus of the foot, a relatively rigid medial stay located in the medial pocket, said medial stay curved to conform to the anatomical shape of the medial portion of the foot and ankle when located in the medial pocket;
   an elongate, narrow lateral pocket formed between the second layer and the outer layer on the lateral side of the base extending from a location near the upper edge of the base downwardly to a position beneath the lateral malleolus of the foot, a relatively rigid lateral stay located in the lateral pocket, said lateral stay curved to conform to the anatomical shape of the lateral portion of the foot and ankle when located in the lateral pocket.

10. The ankle brace of claim 9 wherein: said outer layer is coextensive throughout with the second layer in forming said base, said base having first and second forward edges that come together over the top of the foot and forward of the ankle toward one another, closure means for fixing the first and second forward edges with respect to one another when installed over the foot, said base having a top edge that closes around the lower leg portion and a lower edge that closes around the lower foot when the forward edges are brought together.

11. The ankle brace of claim 10 wherein: said medial and lateral support panels each having a notch located forward of the ankle joint when the base is installed upon a foot.

12. The ankle brace of claim 11 wherein: each support panel is shaped with a relatively straight upper portion extended from beneath the upper edge of the base to a position beneath the ankle in spanning relationship to the ankle, and forwardly curved at the lower portion following the contour of the foot.

13. The ankle brace of claim 12 wherein: each support panel is formed of plastic.

14. The ankle brace of claim 9 wherein: the lateral pocket and the medial pocket each have an open top for removal of the lateral and medial stays.

15. The ankle brace of claim 14 wherein: the lateral pocket and the medial pocket extend vertically downward from the upper edge of the base to a position beneath the malleolus and then curve forwardly following the anatomical contour of the foot, said lateral and medial stays having relatively straight upper portions, outwardly curved mid portions for accommodation of a portion of the malleolus, and inwardly and forwardly curved lower portions in conformance with the anatomical contour of the foot.

16. The ankle brace of claim 15 wherein: means for fixing the first and second forward edges of the base with respect to the foot includes a lace.

17. The ankle brace of claim 16 including: a tongue pivotally connected to one of the forward edges and movable into position covering the front superior foot and ankle portion when the forward edges are brought together.

18. The ankle brace of claim 17 wherein: said first medial and lateral support panels have a porosity of greater than 50 percent.

19. The ankle brace of claim 1 wherein: said medial and lateral support panels have a porosity of greater than 50 percent.

20. An ankle brace comprising:
base means formed of a flexible material and having inner and outer layers and shaped to closely encompass the ankle and proximal foot including the medial and lateral sides of the ankle and foot;
a medial support panel embedded in the base means between the inner and outer layers extending from a location on the lower leg above the ankle, downwardly in spanning relationship to the ankle region to a location beneath the ankle region in the vicinity of the foot, means securing the medial support panel between the inner and outer layers of the base comprised as stitching means sewn through the inner and outer layers of the medial side of the base and the medial support panel and extending back and forth across intermediate portions of the medial support panel between opposite edges thereof;
a lateral support panel embedded between the inner and outer layers of the base on the lateral side of the base, said lateral support panel extending from a location on the lower leg above the ankle, downwardly in spanning relationship to the ankle region to a location beneath the ankle region in the vicinity of the foot, means securing the lateral support panel to the base comprised as stitching means sewn though the inner and outer layers of the lateral side of the base and the lateral support panel and extending back and forth across intermediate portions of the lateral support panel between opposite edges thereof;
said medial and lateral support panels being of a width to extend circumferentially around the ankle from a position rearwardly thereof to a position forward thereof;
each support panel formed of a mesh material having a first set of resilient flexible parallel strands, and a second set of resilient flexible parallel strands perpendicular to the first set and interconnected therewith and defining a plurality of openings such that the support panel has a porosity greater than 50 percent.

21. The ankle brace of claim 20 wherein: said base has first and second forward edges that come toward one another across the front superior foot portion, with an upper edge surrounding the lower ankle portion and a forward edge surrounding the forward foot portion when the first and second forward edges are brought together across the front superior foot portion, and including means securing the first and second edges in place with respect to one another and the foot.

22. The ankle brace of claim 21 wherein: said forward edges have eyelets including a lace trained between the first and second forward edges for securing the edges with respect to one another.

23. The ankle brace of claim 22 wherein: stitching means securing the support panels in place includes a plurality of zig-zag pattern seams.

24. The ankle brace of claim 23 wherein: said medial and lateral support panels each have a notch located forward of the ankle joint when the base is installed upon a foot.

25. The ankle brace of claim 24 wherein: each said support panel is shaped with a relatively straight upper portion extended from beneath the upper edge of the base to a position beneath the ankle in spanning relationship to the ankle, and forwardly curved at the lower portion to follow the contour of the foot.

26. An ankle brace comprising:
base means formed of a flexible material and having an inner layer and a first outer layer and shaped to closely encompass the ankle and proximal foot including medial and lateral sides for encompassing medial and lateral sides of the ankle and foot;
a medial support panel embedded in the base means between the inner and outer layers extending from a location on the lower leg above the ankle, downwardly in spanning relationship to the ankle region to a location beneath the ankle region in the vicinity of the foot, means securing the medial support panel between the inner and outer layers of the base;
a lateral support panel embedded between the inner and outer layers of the base on the lateral side of the base, said lateral support panel extending from a location on the lower leg above the ankle, downwardly in spanning relationship to the ankle region to a location beneath the ankle region in the vicinity of the foot, means securing the lateral support panel to the base;
said medial and lateral support panels being of a width to extend circumferentially around the ankle from a position rearwardly thereof to a position forward thereof;
each support panel formed of a mesh material having a first set of resilient flexible parallel strands, and a second set of resilient flexible parallel strands perpendicular to the first set and interconnected therewith and defining a plurality of openings such that the support panel has a porosity greater than 50 percent;
a second outer layer of flexible sheet-like material secured to the first outer layer in emcompassing relationship to the first outer layer at least on the medial and lateral sides of the base; an elongate, narrow medial pocket formed between the first and second outer layers on the medial side of the base extending from a location near the upper edge of the base downwardly to a position beneath the medial malleolus of the foot, a relatively rigid medial stay located in the medial pocket, said medial stay curved to conform to the anatomical shape of the medial portion of the foot and ankle when located in the medial pocket;
an elongate, narrow lateral pocket formed between the first and second outer layers on the lateral side of the base extending from a location near the upper edge of the base downwardly to a position beneath the lateral malleolus of the foot, a relatively rigid lateral stay located in the lateral pocket, said lateral stay curved to conform to the anatomical shape of the lateral portion of the foot and ankle when located in the lateral pocket.

27. The ankle of claim 26 wherein: said base has first and second forward edges that come together over the top of the foot and forward of the ankle toward one another, closure means for fixing the first and second forward edges with respect to one another when installed over the foot, said base having a top edge that closes around the lower leg portion and a lower edge that closed around the lower foot when the forward edges are brought together.

28. The ankle of claim 27 wherein: said medial and lateral support panels each having a notch located forward of the ankle joint when the base is installed upon a foot.

29. The ankle brace of claim 26 wherein: the lateral pocket and the medial pocket each have an open top for removal of the lateral and medial stays.

30. The ankle brace of claim 26 wherein: the lateral pocket and the medial pocket have open tops for removal of the stays and extend vertically downward from the upper edge of the base to a position beneath the malleolus and then curve forwardly following the anatomical contour of the foot, said lateral and medial stays having relatively straight upper portions, outwardly curved mid portions for accommodation of a portion of the malleolus, and inwardly and forwardly curved lower portions in conformance with the anatomical contour of the foot.

31. The ankle brace of claim 30 wherein: said forward edges have eyelets and said means for fixing the first and second forward edges of the base with respect to the foot includes a lace.

32. The ankle brace of claim 31 including: a tongue pivotally connected to one of the forward edges and movable into position covering the front superior foot and ankle portion when the forward edges are brought together.

* * * * *